United States Patent [19]

Christie

[11] Patent Number: 4,761,437

[45] Date of Patent: Aug. 2, 1988

[54] PROCESS FOR PREPARING FRAGRANCE CHIPS

[76] Inventor: Sharon K. Christie, 23 Narions La., Northport, N.Y. 11768

[21] Appl. No.: 1,684

[22] Filed: Jan. 9, 1987

[51] Int. Cl.$^4$ .......................... A61K 7/46; C11B 9/00
[52] U.S. Cl. .................................. 523/102; 252/174.11
[58] Field of Search ..................... 523/102; 252/174.11

[56] References Cited

U.S. PATENT DOCUMENTS

| | | | |
|---|---|---|---|
| 4,095,031 | 6/1978 | Engle | 523/102 |
| 4,496,467 | 1/1985 | Munteanu et al. | 252/174.11 |
| 4,515,909 | 5/1985 | Sawano et al. | 523/102 |
| 4,541,949 | 9/1985 | Sprecker et al. | 252/174.11 |
| 4,590,111 | 5/1986 | Takeuchi | 428/67 |
| 4,652,400 | 3/1987 | Sprecker | 424/70 |
| 4,678,684 | 7/1987 | Sand | 428/305.5 |

FOREIGN PATENT DOCUMENTS

| | | | |
|---|---|---|---|
| 0026952 | 3/1976 | Japan | 523/102 |
| 0198554 | 11/1983 | Japan | 523/102 |
| 0150171 | 8/1984 | Japan | 523/102 |

*Primary Examiner*—Herbert J. Lilling
*Attorney, Agent, or Firm*—Beehler, Pavitt, Siegemund, Jagger, Martella & Dawes

[57] ABSTRACT

A fragrance chip which incorporates a substantial quantity of liquid fragrance material is prepared by absorbing liquid fragrance material on ethylene vinyl acetate copolymer, melting and shaping the copolymer to produce a solid fragrance chip having the desired shape. Polyolefins and other polymeric materials may be included to achieve the desired physical and fragrance release characteristics.

3 Claims, No Drawings

PROCESS FOR PREPARING FRAGRANCE CHIPS

This invention relates to fragrance chips and the process by which they are prepared. Fragrance chips are solid bodies which emit an odor that is characteristic of a particular fragrance material. Fragrance materials include, for example, perfumes. Perfume fragrance chips according to this invention are solid bodies which emit an odor that is accurately characteristic of a particular perfume or fragrance.

Previously, considerable difficulty had been experienced in preparing and providing shaped fragrance chips, particularly those which had a weight in excess of approximately one gram. Fragrance materials are typically highly complex mixtures of ingredients and they are extremely sensitive to degradation by contact with other materials or by severe processing conditions. Previously, it had been generally impractical to produce shaped fragrance chips which emit the true odor of, for example, delicately compounded perfumes. The chemicals in the body of the chip or the processing conditions under which the shaped chip was produced tended to degrade the characteristics of the perfume. Previous expedients often required that the fragrance be adapted to the characteristics of the solid body or particular processing requirements. The previously proposed expedients generally were only applicable to a few fragrances. It was thus generally impractical to produce shaped fragrance chips which truly represented the more delicate perfumes. Also, previously considerable difficulty was experienced in providing an adequate amount of fragrance material in the solid phase chip. Large quantities of liquid fragrance material were generally difficult or impossible to incorporate in solid phase materials. The formulations utilized in attempting to produce solid fragrance chips often resulted in solid phase chips which could not be placed on a polished organic surface, such as a varnished or lacquered table top, because the materials on the surface of the chip would tend to soften or dissolve the finish. These and other difficulties of the prior art have been overcome according to the present invention.

According to the present invention, a solid phase chip is provided through a process which permits the incorporation of up to approximately 25 weight percent of a liquid fragrance material in a solid phase body comprised of ethylene vinyl acetate copolymer and having a weight in excess of approximately one gram. The physical characteristics of the body and its fragrance release characteristics are tailored by the use of various polymeric materials according to the present invention. The materials and processing conditions through which this solid body is produced are such that the true odor of the fragrance material is emitted in the vapor phase by the fragrance chip. The characteristics of the chip are such that it will not mar a delicate surface when placed thereon. A wide variety of liquid fragrance materials may be utilized in this invention. Modification of these liquid fragrance materials to permit their utilization in this invention by reducing them to powder form or otherwise is not required. The true odor of very delicate fragrance materials is thus available in solid phase fragrance chips. The quantities of fragrance materials which may be incorporated in the solid body according to the present invention provides a long lasting fragrance chip which emits an odor that is truly representative of the fragrance material. The odor is emitted in an amount sufficient to be useful, for example, as a perfume sampling device.

These fragrance chips find particular utility in sampling at retail level of, for example, expensive perfumes. They are conveniently provided in chips which have the general size and configuration of a silver dollar. The fragrance chips according to the present invention may also be utilized to provide a desired scent or odor in an area.

According to the present invention, a solid phase fragrance chip is provided which comprises up to approximately 25 weight percent of fragrance material, which is incorporated in the liquid form, and up to approximately 95 weight percent of solid phase ethylene vinyl acetate copolymer. Various other polymeric materials, such as polyolefins, may be incorporated as described to provide particular characteristics, such as fragrance release, surface finish, hardness, processability in the molten phase, and the like.

In general, the fragrance material is added in the desired weight percent to a dry free-flowing particulate form of ethylene vinyl acetate copolymer. The copolymer is generally in the form of beadlets, having an average particle size of less than one eighth of an inch, but may be in powder form, if desired. The other polymeric materials, if any, are usually added at this time in beadlet form. The fragrance material with the beadlets and the resulting mass is admixed for a considerable period of time, generally from one to six hours. The admixing of this mass takes place at approximately room temperature, below approximately 100 degrees Fahrenheit, and preferably below approximately 80 degrees Fahrenheit. The mixing is continued until the beadlets are again substantially dry and free flowing. The resulting admixture is allowed to stand and season for a considerable period of time, generally at least twelve hours and preferably at least 24 hours. If the beadlets show any tendency to coalesce or stick together during the seasoning period, the admixture is periodically subjected to further mixing and blending during the period of standing. Generally, where required, tumbling or mixing is accomplished at least every twelve hours and preferably every three to six hours. This seasoning and periodic mixing of the admixture is performed over a period of up to approximately three days. Longer times are generally not economically feasible. All of the mixing and seasoning is carried out at approximately room temperature and preferably at temperatures no higher than approximately 80 degrees Fahrenheit. The seasoned admixture is then melted and shaped into the desired configuration and cooled as rapidly as possible so that the admixture is exposed to elevated temperatures for as short a time as possible, preferably from approximately 7 to 15 minutes. In general, the conditions of processing are controlled so that the highest temperature to which the admixture is exposed does not exceed from approximately 280 to 325 degrees Fahrenheit.

In general, the molten phase of the processing is conveniently accomplished in a screw extruder and the solid body is formed to the desired shape by either extrusion or injection molding.

The resulting product emits an odor which is characteristic of the incorporated fragrance material in the vapor phase. The fragrance does not appear as a liquid phase on the surface of the resulting fragrance chip. The exact mechanism involved in the release of the odor has not been determined, but it is believed that the fragrance diffuses in the vapor phase through the solid body. It is believed that the selection and proportioning of the ingredients in the composition, the extended mixing and seasoning of the admixture, coupled with the use of the minimum possible maximum temperature and minimum possible residence or dwell times in the molten phase, all contribute to the production of the unique fragrance chip of the present invention.

All of the various fragrance families are represented by the fragrance materials which may be utilized according to the present invention. The fragrance families include, for example, green notes, floral notes, aldehydic notes, chypre notes, oriental notes, tobacco notes, leather notes, fougere notes and combinations of these notes. In all, the "fragrance organ" which available to a perfumer includes more than 4,000 separate notes and any given perfume may contain more than 100 of these separate notes. The present invention permits the incorporation of complex fragrance materials into a solid body, while at the same time retaining the full and true order of the fragrance material over a substantial period of time. Modification of such complex fragrance materials to accommodate some other solid phase system would be impractical and in most cases impossible.

The quantity of fragrance material which is incorporated in the solid body ranges from approximately 4 to 25 weight percent and preferably from approximately 4 to 15 weight percent. The advantages of this invention are generally not fully realized when quantities of less than approximately 4 weight percent are utilized. Percentages of fragrance material in excess of approximately 20 weight percent become increasingly difficult to successfully incorporate in the solid body and the quality of the odor may degrade due to an excess of base note fragrance materials in the odor. The use of more than approximately 15 weight percent of the fragrance material is not generally required to achieve the desired fragrance emission characteristics. The useful life of the fragrance chip and its fragrance quality is determined in part by the quantity of fragrance material which is incorporated within it, in part by the relative volatility of the fragrance material and in part by the polymeric materials and processing which are used.

The ethylene vinyl acetate copolymer resins which are suitable for use according to the present invention generally contain from approximately 9 to 40 weight percent of vinyl acetate and exhibit melt indexes ranging from 0.3 to 500 dg/min. The softening temperatures of these materials range from approximately 100 to 180 degrees Fahrenheit. These copolymers are preferably utilized without the inclusion of any plasticizers other than the fragrance materials. These copolymers exhibit a very low odor and a clarity which varies from translucent to transparent.

Various formulations have been prepared according to the present invention. These are illustrated in Table I. All parts and percentages referred to herein are by weight and temperatures are in Fahrenheit, unless otherwise indicated.

TABLE I

| Formula No. | 1 | 2 | 3 | 4 | 5 | 6 | 7 | 8 | 9 | 10 | 11 | 12 |
|---|---|---|---|---|---|---|---|---|---|---|---|---|
| EVA[1] wt % | 95 | 90 | 40 | 35 | 30 | 35 | — | 25 | 60 | 80 | 50 | 40 | 20 |
| vinyl acetate wt % | 9 | 18 | 28 | 28 | 28 | 28 | — | 28 | 28 | 39 | 28 | 28 | 28 |
| LDPE[2] wt % | — | — | 50 | 50 | 50 | — | — | — | — | 30 | — | — |
| polypropylene wt % | — | — | — | — | 50 | — | — | — | — | — | 40 | 75 |
| polystyrene wt % | — | — | — | — | — | 65 | 35 | — | — | — | — | — |
| E/MAA[3] wt % | — | — | — | — | 5 | — | — | — | — | 10 | 5 | — |
| polyurethane wt % | — | — | — | — | — | — | — | — | — | — | — | — |
| Fragrance wt % | 5 | 10 | 10 | 15 | 15 | 15 | 10 | 5 | 20 | 10 | 15 | 5 |
| mixing, hrs | 1 | 2 | 2 | 3 | 6 | 2.5 | 3 | 3 | 3 | 4 | — | — |
| seasoning, hrs. | 24 | 24 | 24 | 24 | 24 | 24 | 24 | 24 | 12 | 24 | — | — |
| mixing temp. | 70 | 70 | 70 | 70 | 70 | 70 | 70 | 70 | 70 | 70 | 70 | 70 |
| seasoning temp. | 70 | 70 | 70 | 70 | 70 | 70 | 70 | 70 | 70 | 70 | 70 | 70 |
| dwell time, min. | 13 | 10 | 7 | 8 | 15 | 12 | 10 | 10 | 14 | 13 | 14 | 12 |

Nozzle Temperature (Fahrenheit):

| Formula No. 1 - 307 | Formula No. 7 - 330 |
|---|---|
| 2 - 302 | 8 - 330 |
| 3 - 310 | 9 - 305 |
| 4 - 310 | 10 - 320 |
| 5 - 310 | 11 - 310 |
| 6 - 305 | 12 - 315 |

[1] Ethylene vinyl acetate copolymer
[2] Low density polyethylene, melt point index 20
[3] Ethylene and methacrylic acid copolymer The polymeric materials utilized in the various formulations set forth in Table I are in beadlet form with average particle sizes of less than about one eighth of an inch. Mixing is accomplished in a ribbon mixer. Fragrance chips of approximately three grams in weight are formed by cutting chips off of a continuous strip which is formed by means of a screw extruder. The fragrance chips are formed from continuous extrusions for the sake of convenience. When particular shapes are desired, they are conveniently formed by injection molding techniques.

The percentage of vinyl acetate indicated in the Table I is a percentage of the copolymer and not of the overall mixture.

In Formula No. 1 in Table I, the ethylene vinyl acetate copolymer has a melt point index of 7, in Formula No. 2 it is 8, in No. 9 it is 48 and in the remainder of the Formulations it is 6.

The liquid fragrance in Formulas Nos. 1 and 2 is fruity aldehydic, in No. 3 it is liquid musk, in No. 4 it is liquid oriental, in Nos. 5, 7, 8 and 10 it is liquid green aldehydric floral, in Nos. 6, 11 and 12 it is liquid citrus, and in No. 9 it is liquid chocolate.

The dwell time in Table I is the time required for the material to pass through the screw extruder from the hopper, where it enters at room temperature through the nozzle. The nozzle temperature is the temperature of the molten mass as it exits the nozzle. This is the maximum temperature to which the material is exposed. Most of the dwell time in the screw extruder is spent heating the material to this temperature. The residence time at this temperature is short.

A comparison of Formulations Nos. 1 and 2 indicates that the fragrance release characteristics of No. 1 are slower and physically the chip is somewhat harder than Formula No. 2. In general, the higher the percentage of vinyl acetate in the product, the faster the fragrance release for a given fragrance. The results of these various examples indicate that the preferred range of liquid fragrance material is from approximately 4 to 15 weight percent.

The time required to effect thorough mixing of the fragrance material and the polymeric material to the point where the beadlets are substantially dry and free flowing is largely a function of the liquid fragrance material for a given polymeric material. The less volatile fragrance materials generally require longer mixing times. The ethylene vinyl acetate copolymer is responsible for absorbing the liquid fragrance material during the mixing operation. If, for example, low density polyethylene beadlets are mixed with five percent by weight of fragrance, the beadlets will not be dry and free flowing, even after as much as twelve hours of mixing. Where large percentages of fragrance materials are used, several mixing stages may be required, even where substantial percentages of vinyl acetate are utilized.

The presence of low density polyethylene and polypropylene have an impact on both the physical and the fragrance characteristics of the product. In general, polyolefins give a different texture and feel to the physical product. When incorporated in the admixture, polyolefins tend to result in a chip from which the odor is emitted in substantial quantities for a long period of time, sometimes in excess of a year. Also, the integrity of the fragrance is retained for long periods of time. The two preferred polyolefins, polyethylene and polypropylene, tend to retard the top notes, so that they come off more with the middle notes. The action of the polypropylene is more pronounced in this regard. This action tends to maintain the true character of the fragrance at a substantially constant value for an extended period of time.

The ethylene and methacrylic acid copolymers are very effective in fixing the fragrance so that it emits substantially the same odor for very extended periods of time. The particular copolymer which is preferred for this purpose is a product which is sold under the "Surlyn" trademark by E. I. DuPont de Nemours & Co. (Inc.), Polymer Products Department, Ethylene Polymers Division, Wilmington, Delaware 19898. The Surlyn product which is used in the above formulations is Surlyn No. 8660. The formulations which contain this ethylene methacrylic acid copolymer exhibit very stable fragrance characteristics which have an extended life. The use of this material in quantities of approximately five to ten percent or more, particularly in a molded product, produces a product which has a very elegant physical appearance. It has a shiny smooth non-scuffing surface which can be silk screened or hot stamped. The use of excessive amounts of this material in excess of approximately 15 weight percent, however, requires nozzle temperatures which are above those which can be tolerated by most fragrance materials.

The use of polystyrene also requires elevated working temperatures. This material, even in small quantities, significantly inhibits the fragrance release, so that the product is more of a scented chip which must be brought to the nose to detect the fragrance, than a fragrance-emitting vehicle.

Where fragrance loads of approximately 20 weight percent or more are utilized, the liquid fragrance material tends to plasticize the polymeric material to a substantial degree, so that special tooling and handling may be required. Longer mixing times are generally required, as are multiple mixing operations. The higher concentrations of fragrance material may also tend to degrade the fragrance characteristics of the chip by releasing too fast and allowing the base notes of the fragrance to come through too strongly.

The color of the chip may range from clear to translucent. Inert color additives may be added, if desired.

What have been described are preferred embodiments in which modifications and changes may be made without departing from the spirit and scope of the accompanying claims.

What is claimed is:

1. A process for producing a fragrance material incorporating solid body comprising:
   selecting a liquid fragrance material,
   selecting a substantially dry solid phase ethylene vinyl acetate copolymer in particulate form,
   combining said copolymer and no more than about 25 weight percent of said fragrance material and admixing the resulting mass at no more than about 100 degrees Fahrenheit until said resulting mass is substantially dry,
   allowing the resulting admixture to stand at approximately room temperature for at least 12 hours to produce a seasoned admixture,
   heating said seasoned admixture at a temperature not to exceed approximately 325 degrees Fahrenheit to produce a molten admixture,
   forming the resultant molten admixture into a desired configuration and cooling said molten admixture while maintaining said configuration to produce said fragrance material incorporating solid body.

2. A process of claim 1, including melting said admixture in a screw extruder and injection molding said molten admixture to form said fragrance material incorporating solid body.

3. A process of claim 1 including combining no more than approximately 75 percent by weight of the solid body of low density polyolefin.

* * * * *